(12) United States Patent
Bender et al.

(10) Patent No.: US 8,431,568 B2
(45) Date of Patent: Apr. 30, 2013

(54) AROMATIC HETEROCYCLIC FUSED INDOLOBENZADIAZEPINE HCV NS5B INHIBITORS

(75) Inventors: John A. Bender, Middletown, CT (US); Zhong Yang, Southington, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 287 days.

(21) Appl. No.: 12/922,801

(22) PCT Filed: Mar. 24, 2009

(86) PCT No.: PCT/US2009/038010
§ 371 (c)(1),
(2), (4) Date: Sep. 29, 2010

(87) PCT Pub. No.: WO2009/120650
PCT Pub. Date: Oct. 1, 2009

(65) Prior Publication Data
US 2011/0014154 A1 Jan. 20, 2011

Related U.S. Application Data

(60) Provisional application No. 61/039,961, filed on Mar. 27, 2008.

(51) Int. Cl.
*A61P 31/14* (2006.01)
*A61K 31/551* (2006.01)
*C07D 487/14* (2006.01)

(52) U.S. Cl.
USPC .......................................... 514/219; 540/555

(58) Field of Classification Search .................. 514/219; 540/555
See application file for complete search history.

(56) References Cited

U.S. PATENT DOCUMENTS

| 7,153,848 | B2 | 12/2006 | Hudyma et al. |
| 7,348,425 | B2 | 3/2008 | Hudyma et al. |
| 7,399,758 | B2 | 7/2008 | Meanwell et al. |
| 7,452,876 | B2 | 11/2008 | Yeung et al. |
| 7,456,165 | B2 | 11/2008 | Bergstrom et al. |
| 7,456,167 | B2 | 11/2008 | Bergstrom |
| 7,473,688 | B2 | 1/2009 | Bergstrom et al. |
| 7,521,442 | B2 | 4/2009 | Gentles et al. |
| 7,642,251 | B2 | 1/2010 | Bergstrom et al. |
| 7,652,004 | B2 | 1/2010 | Martin et al. |
| 2009/0275561 | A1 | 11/2009 | Martin et al. |
| 2009/0280083 | A1 | 11/2009 | Martin et al. |
| 2011/0020277 | A1 | 1/2011 | Bender et al. |

FOREIGN PATENT DOCUMENTS

| WO | WO 2005/080399 | 9/2005 |
| WO | WO 2006/046030 | 5/2006 |
| WO | WO 2006/046039 | 5/2006 |
| WO | WO 2007/029029 | 3/2007 |

*Primary Examiner* — Brenda Coleman
(74) *Attorney, Agent, or Firm* — James Epperson

(57) ABSTRACT

The disclosure provides compounds of formula (I), including their salts, as well as compositions and methods of using the compounds. The compounds have activity against hepatitis C virus (HCV) and are useful in treating those infected with HCV.

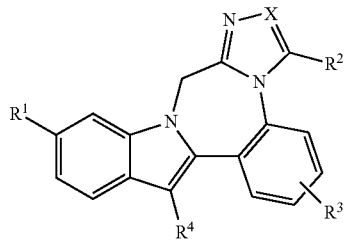

13 Claims, No Drawings

AROMATIC HETEROCYCLIC FUSED INDOLOBENZADIAZEPINE HCV NS5B INHIBITORS

CROSS-REFERENCE TO RELATED APPLICATIONS

This application claims the benefit of U.S. provisional application Ser. No. 61/039,961 filed Mar. 27, 2008.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop further effective compounds for the treatment of HCV infection.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

HCV NS5B inhibitors have been disclosed in U.S. Pat. No. 7,456,165.

DESCRIPTION OF THE INVENTION

The invention encompasses compounds of formula I, including pharmaceutically acceptable salts, and compositions and methods of treatment using these compounds.

One aspect of the invention is a compound of formula I

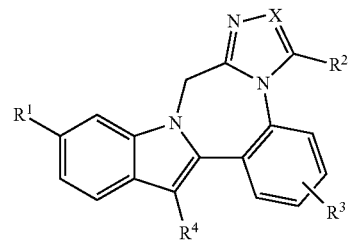

where:
$R^1$ is $CO_2R^5$ or $CONR^6R^7$;
$R^2$ is hydrogen or alkyl;
$R^3$ is hydrogen, halo, alkyl, alkenyl, hydroxy, benzyloxy, or alkoxy;
$R^4$ is cycloalkyl;
$R^5$ is hydrogen or alkyl;
$R^6$ is hydrogen, alkyl, alkylSO$_2$, cycloalkylSO$_2$, haloalkylSO$_2$, $(R^8)(R^9)NSO_2$, or $(R^{10})SO_2$;
$R^7$ is hydrogen or alkyl;
$R^8$ is hydrogen or alkyl;
$R^9$ is hydrogen or alkyl;
$R^{10}$ is azetidinyl, pyrrolidinyl, piperidinyl, piperazinyl, N-(alkyl)piperazinyl, morpholinyl, thiomorpholinyl, homopiperidinyl, or homomorpholinyl;
$R^{11}$ is hydrogen or alkyl; and
X is N or $CR^{11}$
or a pharmaceutically acceptable salt thereof.

Another aspect of the invention is a compound of formula I where $R^1$ is $CO_2R^5$ or $CONR^6R^7$; $R^2$ is hydrogen or alkyl; $R^3$ is hydrogen; $R^4$ is cycloalkyl; $R^5$ is hydrogen; $R^6$ is $(R^8)(R^9)NSO_2$; $R^7$ is hydrogen; $R^8$ is alkyl; $R^9$ is alkyl; $R^{11}$ is hydrogen or alkyl; and X is N or $CR^{11}$; or a pharmaceutically acceptable salt thereof.

Another aspect of the invention is a compound of formula I where $R^1$ is $CO_2H$ or $CONHSO_2NMe_2$; $R^2$ is hydrogen or methyl; $R^3$ is hydrogen; $R^4$ is cyclohexyl; and X is N, CH or CMe; or a pharmaceutically acceptable salt thereof.

Another aspect of the invention is a compound of formula I where $R^1$ is $CONR^6R^7$; $R^6$ is alkyl$SO_2$, cycloalkyl$SO_2$, haloalkyl$SO_2$, $(R^8)(R^9)NSO_2$, or $(R^{10})SO_2$; and $R^7$ is hydrogen.

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is $(R^8)(R^9)_2NSO_2$ or $(R^{10})SO_2$.

Another aspect of the invention is a compound of formula I where X in N.

Another aspect of the invention is a compound of formula I where X is $CR^{11}$.

For a compound of Formula I, the scope of any instance of a variable substituent, including $R^1$, $R^2$, $R^3$, $R^4$, $R^5$, $R^6$, $R^7$, $R^8$, $R^9$, $R^{10}$, $R^{11}$, and X, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "$Et_2O$" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Alkyl 2-bromo-3-cyclohexyl-1H-indole-6-carboxylates can be N-alkylated under mild basic conditions with α-halo acetates to yield alkyl 2-bromo-1-(2-alkoxy-2-oxoethyl)-3-cyclohexyl-1H-indole-6-carboxylates (See Scheme 1). These compounds can be subjected to known coupling reactions with the boronic acids or boronic esters of 2-BOC-protected anilines. The resultant biaryl compounds can be cyclized under standard BOC deprotection conditions with heating to form alkyl 13-cyclohexyl-5H-indolo[1,2-d][1,4]benzodiazepine-6(7H)-one-10-carboxylates. The amide contained within the diazepinone can be converted into a cyclic thioamide with $P_4S_{10}$ under basic conditions at elevated temperatures.

Scheme 1.

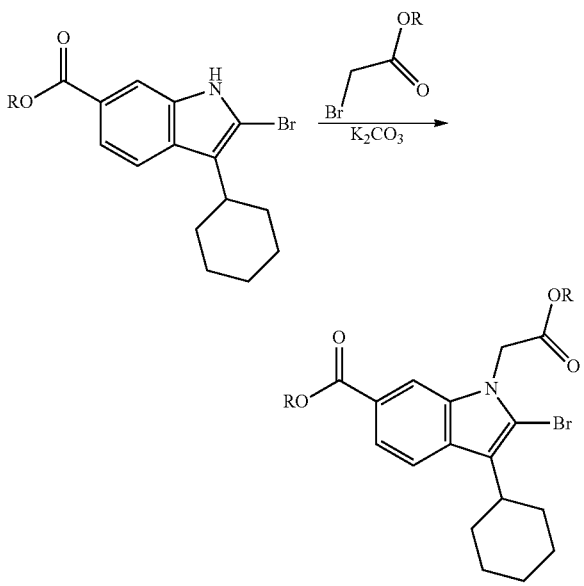

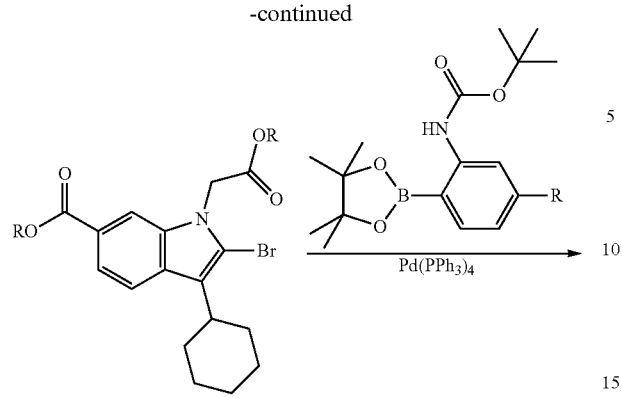
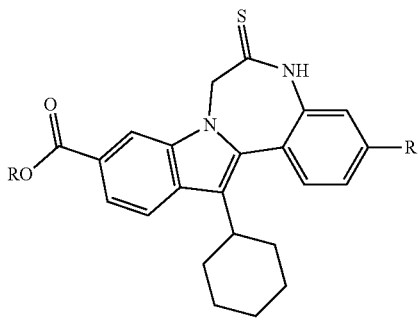

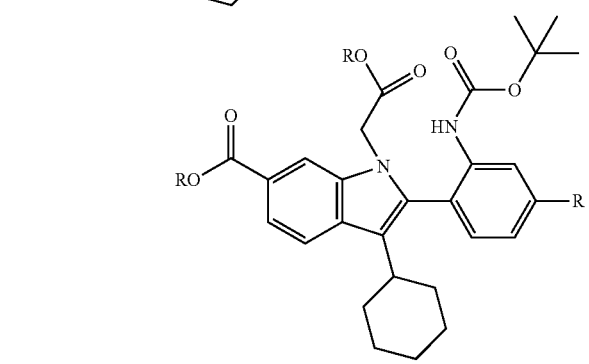

The cyclic thioamides can be useful intermediates in the preparation of some compounds of the invention (See Scheme 2). The reaction of a cyclic thioamide with acyl hydrazines at elevated temperatures is known to form fused 1,2,4-triazoles. Fused imidazoles can be prepared by reacting 1,2-acetal amines with a thioamide intermediate at elevated temperatures through acid catalysis.

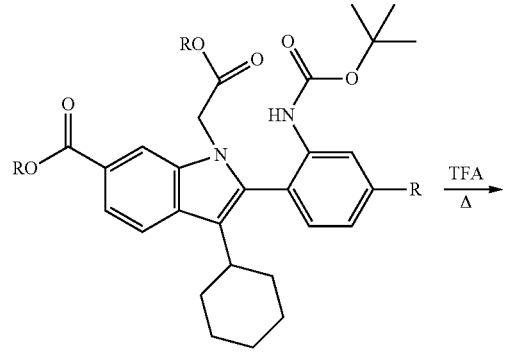

Scheme 2.

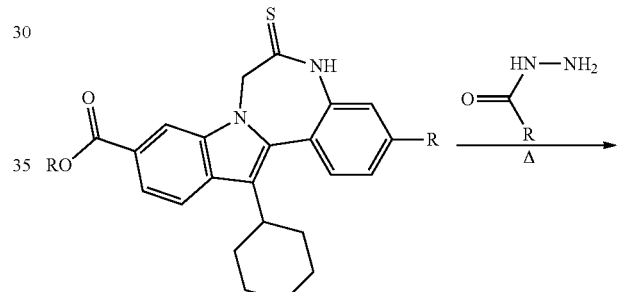

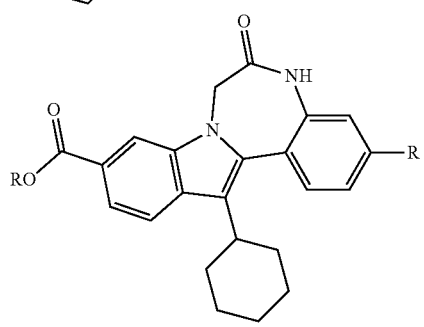
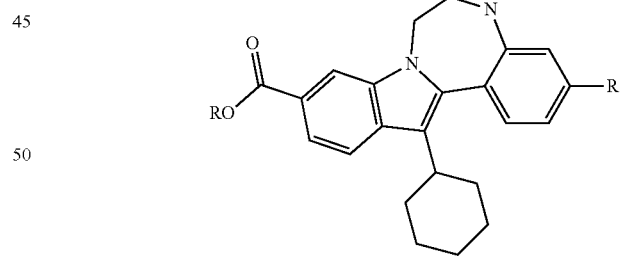

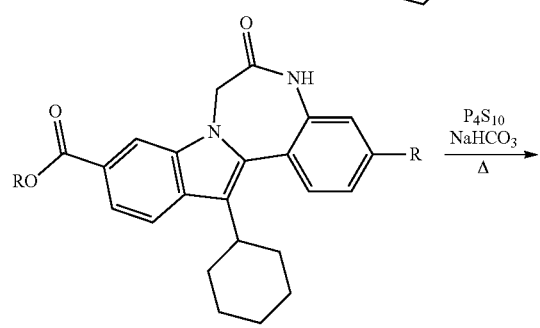
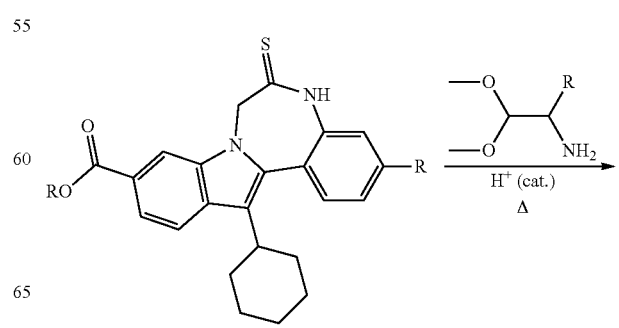

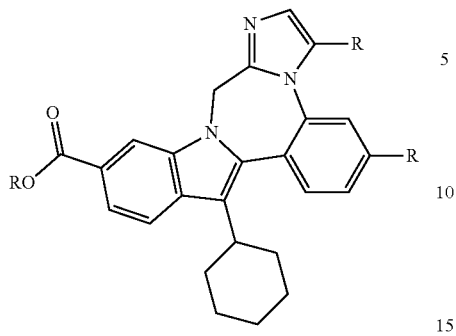

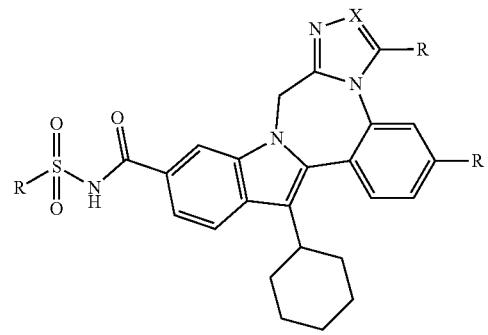

The alkyl ester intermediates can be hydrolyzed to carboxylic acids with the fused five-membered ring heterocycles already in place (See Scheme 3). These compounds can be condensed with a variety of sulfonyl ureas or sulfonamides, using for example, 1,1'-carbonyldiimidazole in combination with 1,8-diazabicyclo[5.4.0]undec-7-ene in anhydrous THF to form acyl sulfamides or acyl sulfonamides.

The order of the reaction sequence that can be used to prepare the compounds of the invention can be altered (See Scheme 4). For example, the alkyl esters of alkyl 2-bromo-3-cyclohexyl-1H-indole-6-carboxylates can be hydrolyzed and converted to acyl sulfamides and/or acyl sulfonamides prior to bis aryl coupling and diazapinone cyclization. The final steps in this sequence involve the formation of the fused heterocycles.

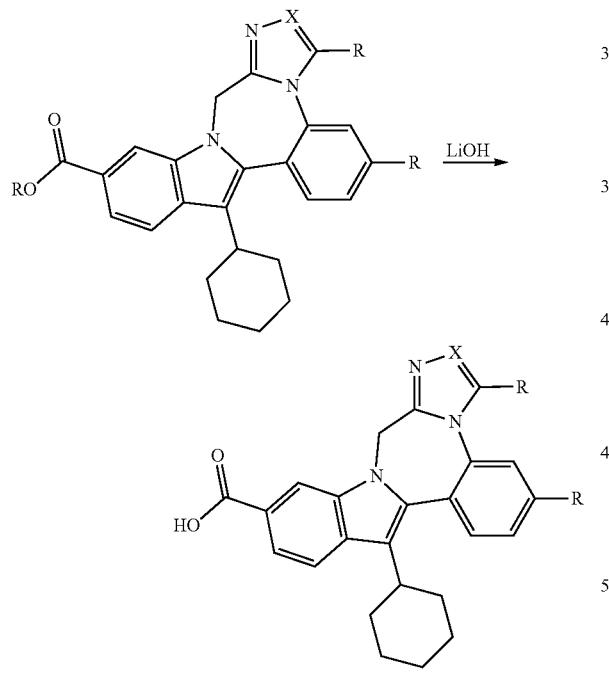

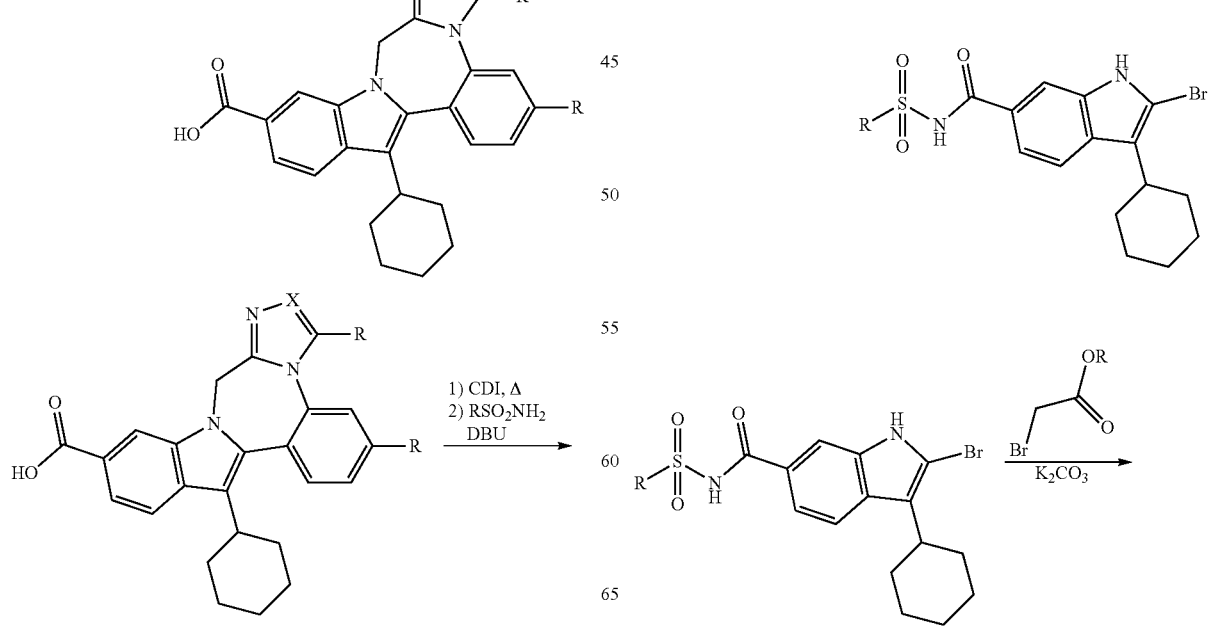

-continued

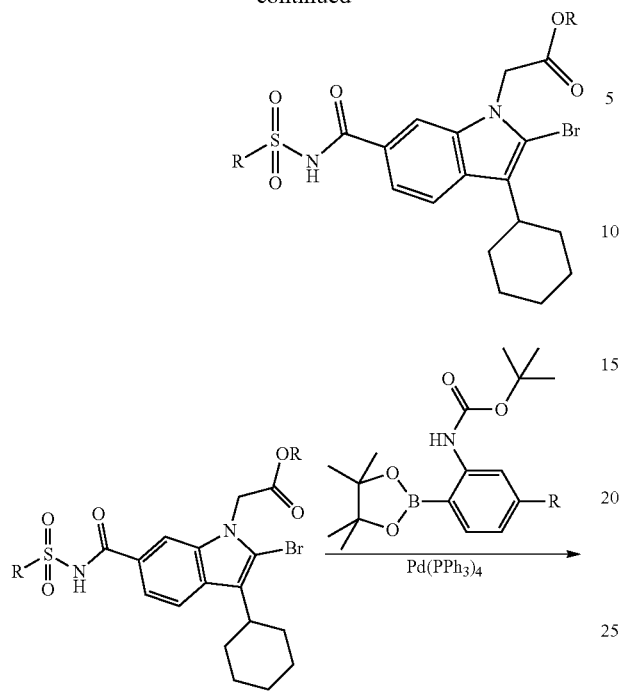

-continued

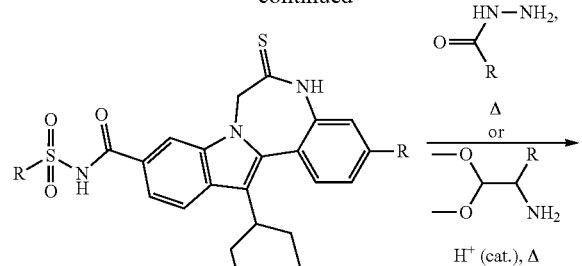

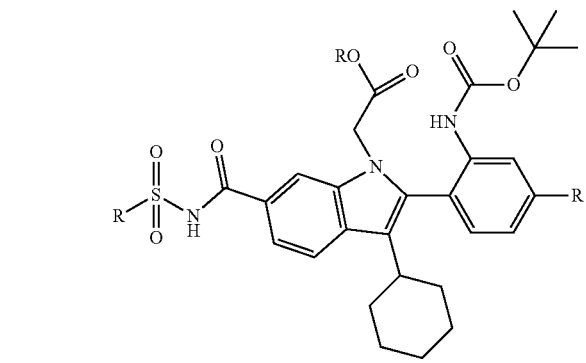

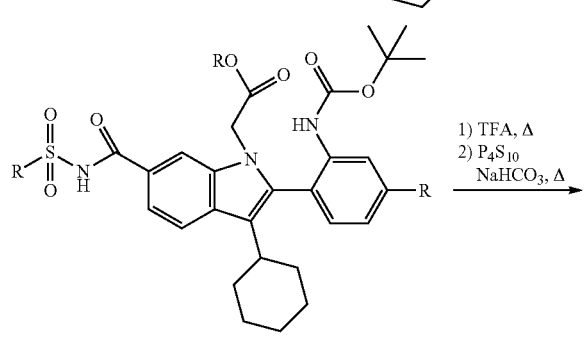

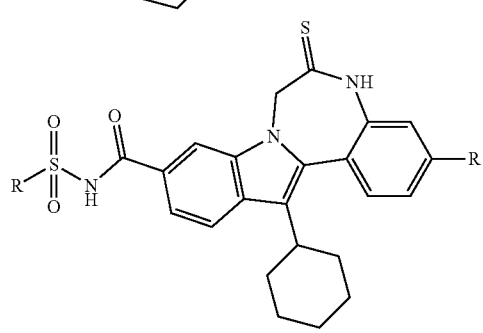

Biological Methods

The compounds demonstrated activity against HCV NS5B as determined in the following HCV RdRp assays.

HCV NS5B RdRp Cloning, Expression, and Purification.

The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp Enzyme Assay.

HCV RdRp genotype 1b assays were run in a final volume of 60 μl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp Enzyme Assay.

A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation.

To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 uM final from a 2 mM stock.

To prepare plates, HCV replicon cells, with or without a *Renilla* luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays.

Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for compounds are reported in Table 1.

TABLE 1

| Example | Structure | $IC_{50}$ (uM) | $EC_{50}$ (uM) |
|---|---|---|---|
| 1 | 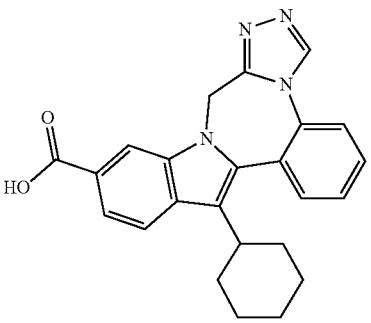 [SMILES: O=C(O)c1ccc2c(C3CCCCC3)c3n(c2c1)Cc1nncn1-c1ccccc1-3] | 0.14 | 0.91 |

TABLE 1-continued

| Example | Structure | IC$_{50}$ (uM) | EC$_{50}$ (uM) |
|---------|-----------|----------------|----------------|
| 2 | 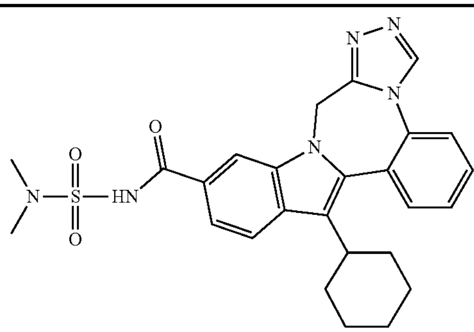 | 0.020 | 0.16 |
| 3 | 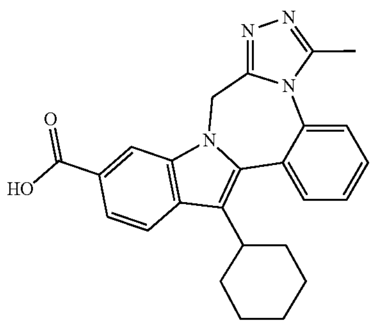 [SMILES: Cc1nnc2n1-c1ccccc1-c1c(C3CCCCC3)c3ccc(C(=O)O)cc3n1C2] | 0.17 | 0.77 |
| 4 | 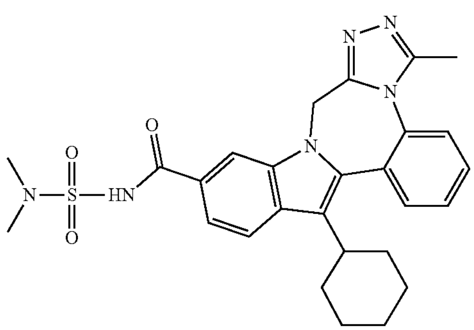 [SMILES: Cc1nnc2n1-c1ccccc1-c1c(C3CCCCC3)c3ccc(C(=O)NS(=O)(=O)N(C)C)cc3n1C2] | 0.054 | 0.32 |
| 5 | 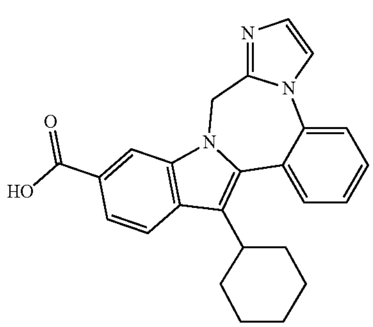 [SMILES: O=C(O)c1ccc2c(C3CCCCC3)c3n(c2c1)Cc1nccn1-c1ccccc1-3] | 0.026 | 0.74 |
| 6 | 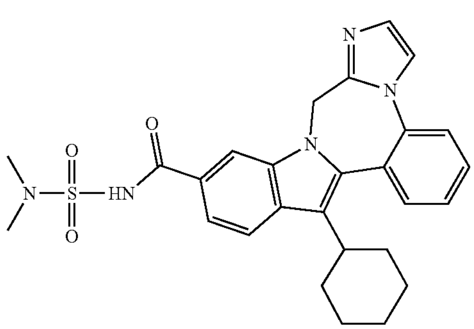 [SMILES: CN(C)S(=O)(=O)NC(=O)c1ccc2c(C3CCCCC3)c3n(c2c1)Cc1nccn1-c1ccccc1-3] | 0.019 | 0.39 |

TABLE 1-continued

| Example | Structure | IC$_{50}$ (uM) | EC$_{50}$ (uM) |
|---|---|---|---|
| 7 | 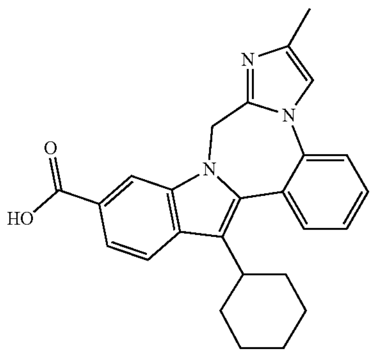 [SMILES: Cc1cn2c(n1)Cn1c(c(C3CCCCC3)c3ccc(C(=O)O)cc31)-c1ccccc1-2] | 0.13 | 2.85 |
| 8 | 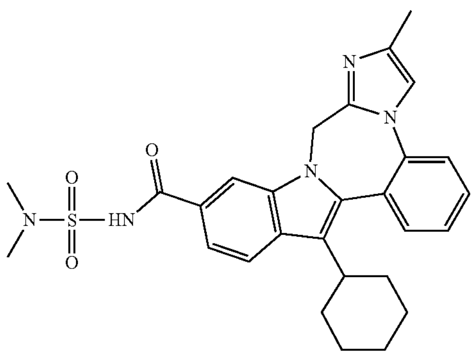 [SMILES: Cc1cn2c(n1)Cn1c(c(C3CCCCC3)c3ccc(C(=O)NS(=O)(=O)N(C)C)cc31)-c1ccccc1-2] | 0.033 | 0.71 |

A > 0.5 µM; B 0.02 µM-0.5 µM; C < 0.02 µM but an exact value was not determined; IC$_{50}$ values were determined using the preincubation protocol.
EC50 values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound of formula I, or a pharmaceutically acceptable salt thereof, and a pharmaceutically acceptable carrier.

Another aspect of the invention is the use of a compound of formula I in the manufacture of a medicament for the treatment of hepatitis C.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of formula I, or a pharmaceutically acceptable salt thereof, a pharmaceutically acceptable carrier, and an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound of formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of formula I, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
| --- | --- | --- |
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |

TABLE 2-continued

| Brand Name | Type of Inhibitor or Target | Source Company |
| --- | --- | --- |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/ Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

DESCRIPTION OF SPECIFIC EMBODIMENTS

Abbreviations used in the schemes generally follow conventions used in the art. Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL," for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Unless otherwise specified, analytical LCMS data on the following intermediates and examples were acquired using the following columns and conditions. Stop time: Gradient time+1 minute; Gradient time: 2 minutes (unless otherwise noted). Starting conc: 0% B unless otherwise noted; Ending conc: 100% B; Eluent A: 10% MeOH/90% H$_2$O with 0.1% TFA; Eluent B: 90% MeOH/10% H$_2$O with 0.1% TFA; Column: Phenomenex 10μ 4.6×50 mm C18.

Preparative HPLC data. Gradient: Linear over 20 min. unless otherwise noted; Starting conc: 15% B unless otherwise noted; Ending conc: 100% B; Eluent A: 10% MeOH/90% H$_2$O with 0.1% TFA; Eluent B: 90% MeOH/10% H$_2$O with 0.1% TFA; Column: Phenomenex Luna C$_{18}$ 10μ30×100 mm.

Intermediate 1

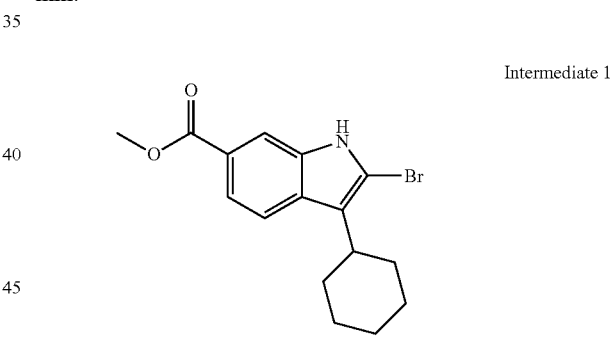

1H-Indole-6-carboxylic acid, 2-bromo-3-cyclohexyl-, Methyl Ester.

Freshly recrystallized pyridinium tribromide (recrystallization from hot AcOH (5 mL per 1 g), rinsed with cold AcOH and dried under high vacuum over KOH) was added in portions (over 10 min.) to a stirring solution of methyl 3-cyclohexyl-1H-indole-6-carboxylate (60 g, 233 mmol) (prepared using procedures describe in WO2004/065367) in CHCl$_3$/ THF (1:1, 1.25 L) at 2° C. The reaction solution was stirred at 0-5° C. for 2.5 h, and washed with sat. aq. NaHSO$_3$ (1 L), 1N HCl (1 L) and brine (1 L). The organic layer was dried (MgSO$_4$) and concentrated. The resulting red oil was diluted with Et$_2$O and concentrated. The resulting pink solid was dissolved into Et$_2$O (200 mL) treated with hexanes (300 mL) and partially concentrated. The solids were collected by filtration and rinsed with hexanes. The mother liquor was concentrated to dryness and the procedure repeated. The solids were combined to yield 1H-indole-6-carboxylic acid, 2-bromo-3-cyclohexyl-, methyl ester (64 g, 190 mmol, 82%)

as a fluffy pink solid, which was used without further purification. $^1$H NMR (300 MHz, CDCl$_3$) δ 1.50-1.27 (m, 3H), 1.98-1.72 (m, 7H), 2.82 (tt, J=3.7, 11.7 Hz, 1H), 3.92 (s, 3H), 7.69 (d, J=8.8 Hz, 1H), 7.74 (dd, J=1.4, 8.8 Hz, 1H), 8.03 (d, J=1.4 Hz, 1H), 8.47 (br s, 1H). $^{13}$C NMR (75 MHz, CDCl$_3$) δ 26.1, 27.0 (2), 32.2 (2), 37.0, 52.1, 110.7, 112.8, 118.7, 120.3, 120.8, 123.1, 130.2, 135.6, 168.2. LCMS: m/e 334 (M−H)$^-$, ret time 3.34 min., 4 minute gradient. Stop time: 5 minutes; Gradient time: 4 minutes; Starting conc: 0% B; Ending conc: 100% B; Eluent A: 5% CH$_3$CN/95% H$_2$O with 10 mM NH$_4$OAc; Eluent B: 95% CH$_3$CN/5% H$_2$O with 10 mM NH$_4$OAc; Column: Phenomenex 10μ 4.6×50 mm C18.

Intermediate 2

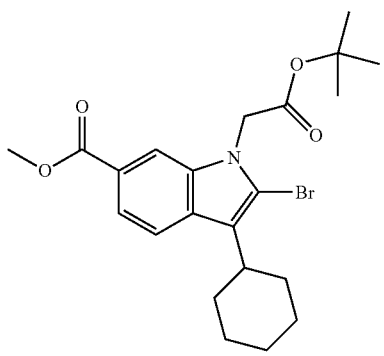

Methyl 2-bromo-1-(2-tert-butoxy-2-oxoethyl)-3-cyclohexyl-1H-indole-6-carboxylate To a solution of methyl 2-bromo-3-cyclohexyl-1H-indole-6-carboxylate (10 g, 30 mmol) in DMF (200 mL) was added tent-butyl 2-bromoacetate (29 g, 150 mmol) and then K$_2$CO$_3$ (25 g, 180 mmol) and the reaction mixture was stirred at rt for 4 h. H$_2$O (250 mL) was added to the mixture and the resulting precipitate was collected by filtration, washed with H$_2$O, and dried under N$_2$ to yield methyl 2-bromo-1-(2-tert-butoxy-2-oxoethyl)-3-cyclohexyl-1H-indole-6-carboxylate (14 g, 30 mmol, quant.) as a white solid, which was used without further purification. LCMS: m/e 450 (M+H)$^+$, ret time 2.44 min.

Intermediate 3

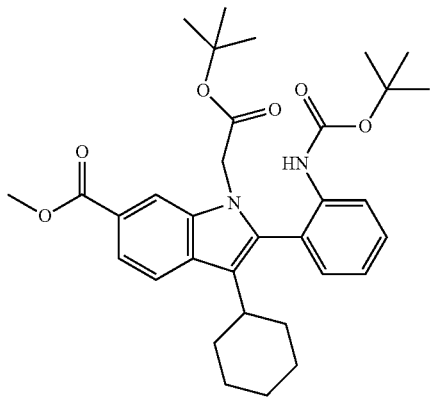

Methyl 1-(2-tert-butoxy-2-oxoethyl)-2-(2-(tert-butoxycarbonylamino)phenyl)-3-cyclohexyl-1H-indole-6-carboxylate To a solution of methyl 2-bromo-1-(2-tert-butoxy-2-oxoethyl)-3-cyclohexyl-1H-indole-6-carboxylate (5.0 g, 11 mmol), (2-BOC-aminophenyl)boronic acid pinacol ester (5.3 g, 16 mmol), and tetrakis (triphenylphosphine)-palladium (0) (1.3 g, 1.1 mmol) in toluene/EtOH (1:1, 80 mL) was added Na$_2$CO$_3$ (3.0 g, 28 mmol), aq. LiCl (2.0M, 22 mL, 44 mmol) and H$_2$O (5 mL). The mixture was refluxed at 100° C. for 2 h, and then the organic solvents were removed under vacuum. The residue is partitioned between EtOAc and water and the organic layer was dried (MgSO$_4$), filtered and concentrated to dryness. The residue was purified by silica gel chromatography (SiO$_2$, EtOAc in hexanes, 5%~40%) to yield methyl 1-(2-tert-butoxy-2-oxoethyl)-2-(2-(tert-butoxycarbonylamino)phenyl)-3-cyclohexyl-1H-indole-6-carboxylate (5.7 g, 10 mmol, 92%) as white solid. LCMS: m/e 563 (M+H)$^+$, ret time 2.52 min.

Intermediate 4

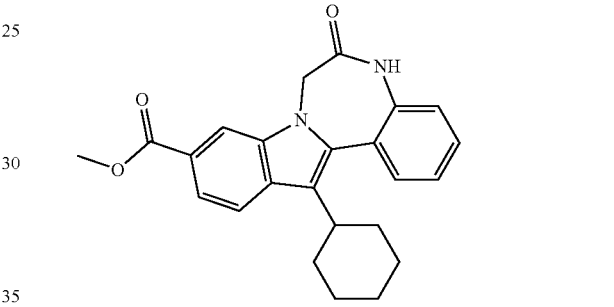

Methyl 13-cyclohexyl-5H-indolo[1,2-d][1,4]benzodiazepine-6(7H)-one-10-carboxylase TFA (5 mL) was added to a solution of methyl 1-(2-tert-butoxy-2-oxoethyl)-2-(2-(tert-butoxycarbonylamino)phenyl)-3-cyclohexyl-1H-indole-6-carboxylate (5.6 g, 10 mmol) in toluene (90 mL) and heated at 100° C. for 1 h. The reaction mixture was allowed to cool and then was carefully poured into a solution of NaHCO$_3$ (10 g) in H$_2$O (200 mL) while stirring. The resulting white precipitate was collected by filtration, flushed with water and EtOAc and dried under N$_2$ to yield methyl 13-cyclohexyl-5H-indolo[1,2-d][1,4]benzodiazepine-6(7H)-one-10-carboxylate (2.9 g, 7.5 mol, 75%) as white solid. LCMS: m/e 389 (M+H)$^+$, ret time 2.22 min.

Intermediate 5

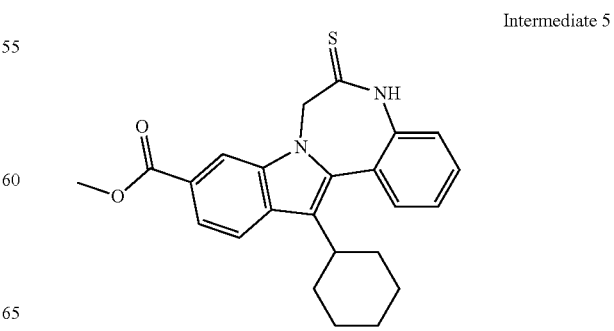

Methyl 13-cyclohexyl-5H-indolo[1,2-d][1,4]benzodiazepine-6(7H)-thione-10-carboxylate P₄S₁₀ (352 mg, 0.791 mmol) and NaHCO₃ (554 mg, 6.60 mmol) were added to a solution of methyl 13-cyclohexyl-5H-indolo[1,2-d][1,4]benzodiazepine-6(7H)-one-10-carboxylate (511 mg, 1.32 mmol) in dioxane (10 mL). The reaction mixture was heated at 100° C. for 1 h, cooled to rt, and diluted with the dropwise addition of H₂O (~20 mL) while stirring. The resulting yellow precipitate was allowed to settle for 1 h, collected by filtration, flushed with water and dried under N₂ to yield methyl 13-cyclohexyl-5H-indolo[1,2-d][1,4]benzodiazepine-6(7H)-thione-10-carboxylate (528 mg, 1.31 mmol, 99%) as yellow solid, which was used without further purification. LCMS: 405 (M+H)⁺, ret time 2.26 min.

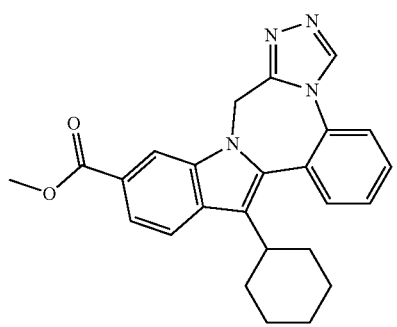

Intermediate 6

Methyl 10-cyclohexyl-4H-indolo[1,2-d][1,2,4]triazolo[4,3-a][1,4]benzodiazepine-7-carboxylate A mixture of methyl 13-cyclohexyl-5H-indolo[1,2-d][1,4]benzodiazepine-6(7H)-thione-10-carboxylate (144 mg, 0.356 mmol) and formic hydrazide (108 mg, 1.80 mmol) in n-BuOH (4 mL) was heated at 140° C. with microwave irradiation for 2 h, cooled, diluted with DMSO and MeOH and purified by prep HPLC (MeOH/H₂O with 10 mM TFA buffer) to yield methyl 10-cyclohexyl-4H-indolo[1,2-d][1,2,4]triazolo[4,3-a][1,4]benzodiazepine-7-carboxylate (66.2 mg, 0.161 mmol, 45%) as a light pink solid. ¹H NMR (500 MHz, CD₃OD) δ 1.17-1.28 (m, 1H), 1.39-1.55 (m, 3H), 1.74-1.85 (m, 2H), 1.94-2.24 (m, 4H), 2.86-2.97 (m, 1H), 3.98 (s, 3H), 5.11 (d, J=15.9 Hz, 1H), 6.06 (d, J=15.9 Hz, 1H), 7.70-7.81 (m, 4H), 7.82-7.86 (m, 1H), 7.96 (d, J=8.2 Hz, 1H), 8.41 (s, 1H), 9.04 (s, 1H). LCMS: m/e 413 (M+H)⁺, ret time 2.16 min.

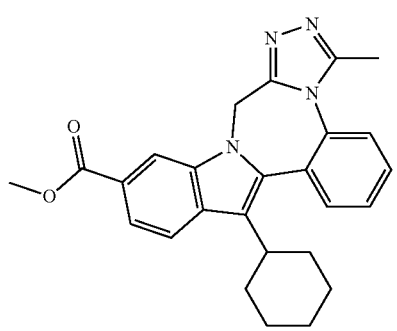

Intermediate 7

Methyl 10-cyclohexyl-1-methyl-4H-indolo[1,2-d][1,2,4]triazolo[4,3-a][1,4]benzodiazepine-7-carboxylate A mixture of methyl 13-cyclohexyl-5H-indolo[1,2-d][1,4]benzodiazepine-6(7H)-thione-10-carboxylate (385 mg, 0.953 mmol) and acetic hydrazide (353 mg, 4.77 mmol) in n-BuOH (7 mL) was heated at 140° C. with microwave irradiation for 2 h. The reaction mixture was diluted with DMSO and MeOH and purified by prep HPLC (MeOH/H₂O with 10 mM TFA buffer) to yield methyl 10-cyclohexyl-1-methyl-4H-indolo[1,2-d][1,2,4]triazolo[4,3-a][1,4]benzodiazepine-7-carboxylate (180 mg, 0.422 mmol, 44%) as a white solid. ¹H NMR (500 MHz, CD₃OD) δ 1.20-1.32 (m, 1H), 1.36-1.60 (m, 3H), 1.73-1.85 (m, 2H), 1.94-2.20 (m, 4H), 2.65 (s, 3H), 2.90-3.01 (m, 1H), 3.97 (s, 3H), 5.02 (d, J=15.6 Hz, 1H), 5.99 (d, J=15.9 Hz, 1H), 7.72-7.84 (m, 5H), 7.96 (d, J=8.6 Hz, 1H), 8.39 (s, 1H). LCMS: m/e 427 (M+H)⁺, ret time 2.15 min.

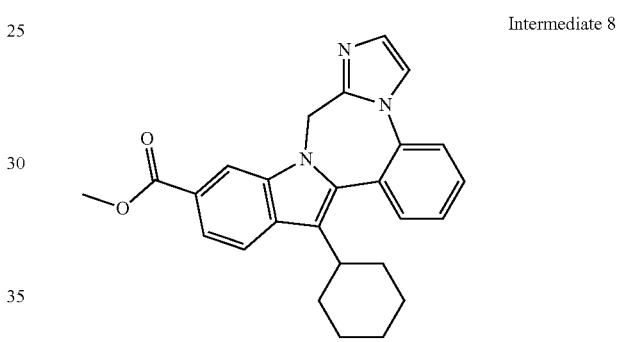

Intermediate 8

Methyl 10-cyclohexyl-4H-imidazo[1,2-a]indolo[1,2-d][1,4]benzodiazepine-7-carboxylate 2,2-Dimethoxyethanamine (260 mg, 2.5 mmol) and p-toluenesulfonic acid monohydrate (94 mg, 0.5 mmol) were added to a solution of methyl 13-cyclohexyl-5H-indolo[1,2-d][1,4]benzodiazepine-6(7H)-thione-10-carboxylate (200 mg, 0.50 mmol) in n-BuOH (4 mL). The reaction mixture was heated at 130° C. with microwave irradiation for 1 h, and then additional p-toluenesulfonic acid monohydrate (380 mg, 2.0 mmol) was added, and the mixture was heated at 130° C. with microwave irradiation for another 1 h. The reaction was diluted with MeOH and DMSO, and purified by prep HPLC (MeOH/H₂O with 10 mM TFA buffer) to yield methyl 10-cyclohexyl-4H-imidazo[1,2-a]indolo[1,2-d][1,4]benzodiazepine-7-carboxylate (37 mg, 0.090 mmol, 18%) as an off white solid. ¹H NMR (500 MHz, CD₃OD) δ 1.15-1.32 (m, 1H), 1.35-1.59 (m, 3H), 1.73-1.84 (m, 2H), 1.94-2.22 (m, 4H), 2.84-3.00 (m, 1H), 3.98 (s, 3H), 5.16 (d, J=16.1 Hz, 1H), 6.02 (d, J=16.1 Hz, 1H), 7.44 (d, J=1.8 Hz, 1H), 7.75-7.90 (m, 5H), 7.92 (d, J=1.8 Hz, 1H), 7.98 (d, J=8.8 Hz, 1H), 8.39 (s, 1H). LCMS: m/e 412 (M+H)⁺, ret time 2.00 min.

Intermediate 9

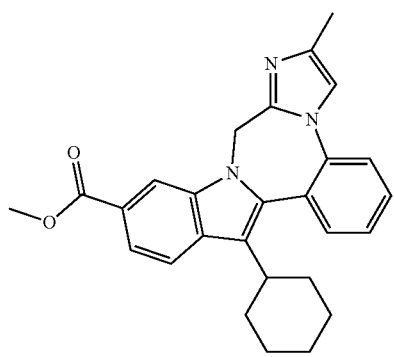

Methyl 10-cyclohexyl-2-methyl-4H-imidazo[1,2-a]
indolo[1,2-d][1,4]benzodiazepine-7-carboxylate 1,1-Dimethoxypropan-2-amine (330 mg, 2.8 mmol) and p-toluenesulfonic acid monohydrate (590 mg, 3.1 mmol) were added to a solution of methyl 13-cyclohexyl-5H-indolo[1,2-d][1,4]benzodiazepine-6(7H)-thione-10-carboxylate (25 0 mg, 0.62 mmol) in n-BuOH (5 mL) The reaction mixture was heated at 130° C. with microwave irradiation for 6 h, cooled to rt, diluted with MeOH and DMSO and purified by prep HPLC (MeOH/H$_2$O with 10 mM TFA buffer) to yield methyl 10-cyclohexyl-2-methyl-4H-imidazo[1,2-a]indolo[1,2-d][1,4]benzodiazepine-7-carboxylate (78 mg, 0.18 mmol, 30%) as a light orange solid. $^1$H NMR (300 MHz, CD$_3$OD) δ 1.14-1.30 (m, 1H), 1.39-1.57 (m, 3H), 1.73-1.84 (m, 2H), 1.93-2.19 (m, 4H), 2.36 (s, 3H), 2.81-2.97 (m, 1H), 3.97 (s, 3H), 5.20 (d, J=16.5 Hz, 1H), 6.06 (d, J=16.5 Hz, 1H), 7.74 (s, 1H), 7.76-7.91 (m, 5H), 7.97 (d, J=8.4 Hz, 1H), 8.38 (s, 1H). LCMS: m/e 426 (M+H)$^+$, ret time 1.80 min.

Example 1

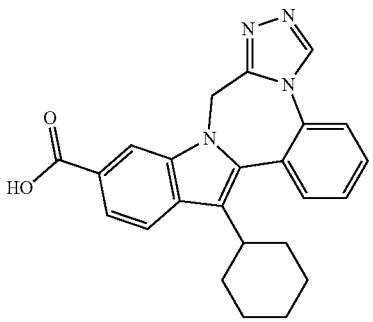 [SMILES: O=C(O)c1ccc2c(C3CCCCC3)c3n(c2c1)Cc1nncn1-c1ccccc1-3]

10-Cyclohexyl-4H-indolo[1,2-d][1,2,4]triazolo[4,3-a][1,4]benzodiazepine-7-carboxylic acid To a solution of methyl 10-cyclohexyl-4H-indolo[1,2-d][1,2,4]triazolo[4,3-a][1,4]benzodiazepine-7-carboxylate (66 mg, 0.16 mmol) in THF (6 mL) and MeOH (3 mL), was added aq NaOH (1.0N, 1.5 mL, 1.5 mmol), and the mixture was heated at 70° C. for 2 h. The solvents were removed, and the white solid residue was washed with water and EtOAc, isolated by centrifuge and dried under vacuum to yield crude 10-cyclohexyl-4H-indolo[1,2-d][1,2,4]triazolo[4,3-a][1,4]benzodiazepine-7-carboxylic acid (54 mg, 0.14 mmol, 85%) as a white solid, which was used without further purification. $^1$H NMR (500 MHz, d$_6$-DMSO) δ 1.07-1.19 (m, 1H), 1.34-1.46 (m, 3H), 1.65-1.75 (m, 2H), 1.86-2.12 (m, 4H), 2.73-2.84 (m, 1H), 5.04 (d, J=15.9 Hz, 1H), 5.93 (d, J=15.9 Hz, 1H), 7.63-7.74 (m, 5H), 7.79-7.85 (m, 1H), 8.18 (s, 1H), 9.08 (s, 1H). LCMS: m/e 399 (M+H)$^+$, ret time 2.02 min.

Example 2

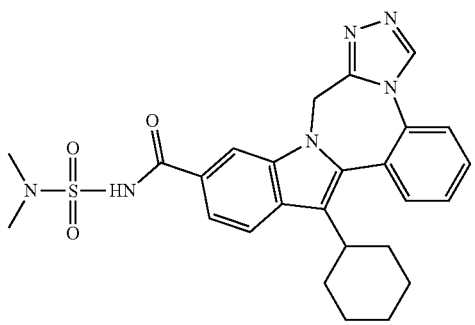 [SMILES: CN(C)S(=O)(=O)NC(=O)c1ccc2c(C3CCCCC3)c3n(c2c1)Cc1nncn1-c1ccccc1-3]

10-Cyclohexyl-N-((dimethylamino)sulfonyl)-4H-indolo[1,2-d][1,2,4]triazolo[4,3-a][1,4]benzodiazepine-7-carboxamide To a solution of 10-cyclohexyl-4H-indolo[1,2-d][1,2,4]triazolo[4,3-a][1,4]benzodiazepine-7-carboxylic acid (50 mg, 0.13 mmol) and N,N-dimethylsulfamide (78 mg, 0.63 mmol) in DMA (2 mL), was added DMAP (77 mg, 0.63 mmol) and then EDCI-HCl (96 mg, 0.50 mmol). The mixture was stirred at 45° C. overnight, diluted with DMSO and MeOH and purified by prep HPLC (MeOH/H$_2$O with 10 mM TFA buffer) to yield 10-cyclohexyl-N-((dimethylamino)sulfonyl)-4H-indolo[1,2-d][1,2,4]triazolo[4,3-a][1,4]benzodiazepine-7-carboxamide (20 mg, 0.040 mmol, 31%) as light pink solid. $^1$H NMR (500 MHz, CD$_3$OD) δ 1.16-1.26 (m, 1H), 1.39-1.55 (m, 3H), 1.73-1.83 (m, 2H), 1.93-2.22 (m, 4H), 2.86-2.96 (m, 1H), 3.04 (s, 6H), 5.14 (d, J=15.9 Hz, 1H), 6.05 (d, J=15.9 Hz, 1H), 7.66 (dd, J=8.55, 1.5 Hz, 1H), 7.72-7.80 (m, 3H), 7.82-7.87 (m, 1H), 7.99 (d, J=8.5, 1H), 8.34 (s, 1H), 9.08 (s, 1H). LCMS: m/e 505 (M+H)$^+$, ret time 1.94 min.

Example 3

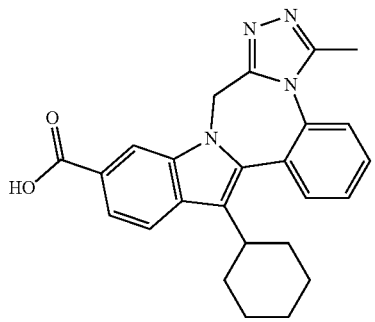 [SMILES: Cc1nnc2n1-c1ccccc1-c1c(C3CCCCC3)c3ccc(C(=O)O)cc3n1C2]

10-Cyclohexyl-1-methyl-4H-indolo[1,2-d][1,2,4]triazolo[4,3-a][1,4]benzodiazepine-7-carboxylic acid To a solution of methyl 10-cyclohexyl-1-methyl-4H-indolo[1,2-d][1,2,4]triazolo[4,3-a][1,4]benzodiazepine-7-carboxylate (173 mg, 0.406 mmol) in THF (7 mL) and MeOH (3.5 mL), was added aq NaOH (1.0N, 1.8 mL, 1.8 mmol). The reaction mixture was heated at 70° C. for 2 h and the solvents were removed. The resulting white solid residue was washed with water, isolated by centrifuge and dried under $N_2$ to yield 10-cyclohexyl-1-methyl-4H-indolo[1,2-d][1,2,4]triazolo[4,3-a][1,4]benzodiazepine-7-carboxylic acid (132 mg, 0.320 mmol, 79%) as a white solid, which was used without further purification. $^1$H NMR (500 MHz, $d_6$-DMSO) δ 1.13-1.24 (m, 1H), 1.35-1.51 (m, 3H), 1.66-1.75 (m, 2H), 1.85-2.08 (m, 4H), 2.48 (s, 3H), 2.79-2.89 (m, 1H), 4.90 (d, J=15.6 Hz, 1H), 5.80 (d, J=15.6 Hz, 1H), 7.65-7.72 (m, 5H), 7.78-7.83 (m, 1H), 8.15 (s, 1H). LCMS: m/e 413 (M+H)$^+$, ret time 2.01 min.

Example 4

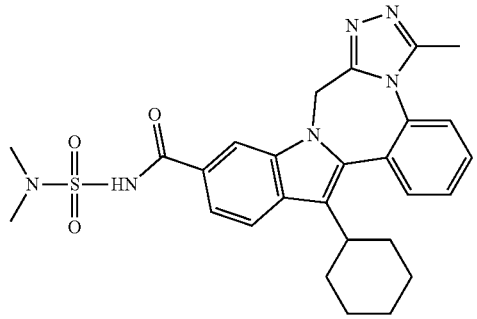 [SMILES: Cc1nnc2n1-c1ccccc1-c1c(C3CCCCC3)c3ccc(C(=O)NS(=O)(=O)N(C)C)cc3n1C2]

10-Cyclohexyl-N-((dimethylamino)sulfonyl)-1-methyl-4H-indolo[1,2-d][1,2,4]triazolo[4,3-a][1,4]benzodiazepine-7-carboxamide To a solution of 10-cyclohexyl-1-methyl-4H-indolo[1,2-d][1,2,4]triazolo[4,3-a][1,4]benzodiazepine-7-carboxylic acid (54 mg, 0.13 mmol) and N,N-dimethylsulfamide (81 mg, 0.65 mmol) in DMA (2 mL), was added DMAP (80 mg, 0.65 mmol), and EDCI-HCl (100 mg, 0.52 mmol). The reaction mixture was stirred at 60° C. for 2 h, cooled to rt, diluted with DMSO and MeOH and purified by prep HPLC (MeOH/H$_2$O with 10 mM TFA buffer) to yield 10-cyclohexyl-N-((dimethylamino)sulfonyl)-1-methyl-4H-indolo[1,2-d][1,2,4]triazolo[4,3-a][1,4]benzodiazepine-7-carboxamide (29 mg, 0.056 mmol, 43%) as a bright yellow solid. $^1$H NMR (500 MHz, CD$_3$OD) δ 1.22-1.34 (m, 1H), 1.41-1.62 (m, 3H), 1.77-1.85 (m, 2H), 1.95-2.18 (m, 4H), 2.71 (s, 3H), 2.90-3.00 (m, 1H), 3.05 (s, 6H), 5.09 (d, J=15.9 Hz, 1H), 6.03 (d, =15.9 Hz, 1H), 7.67 (dd, J=8.2, 1.5 Hz, 1H), 7.79-7.87 (m, 4H), 8.00 (d, J=8.6 Hz, 1H), 8.33 (s, 1H). LCMS: m/e 519 (M+H)$^+$, ret time 1.96 min.

Example 5

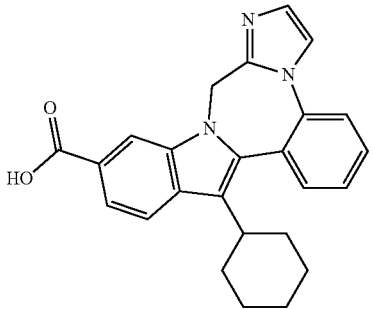 [SMILES: O=C(O)c1ccc2c(C3CCCCC3)c3n(c2c1)Cc1nccn1-c1ccccc1-3]

10-Cyclohexyl-4H-imidazo[1,2-a]indolo[1,2-d][1,4]benzodiazepine-7-carboxylic acid To a solution of methyl 10-cyclohexyl-4H-imidazo[1,2-a]indolo[1,2-d][1,4]benzodiazepine-7-carboxylate (34 mg, 0.083 mmol) in THF (1.5 mL) and MeOH (1 mL), was added aq NaOH (1.0N, 0.4 mL, 0.4 mmol). The reaction mixture was heated at 70° C. for 2 h, cooled to rt, neutralized with aq HCl (1.0N, 0.4 mL) and concentrated to dryness. The solid residue was dissolved into MeOH, filtered, concentrated and dried under $N_2$ to yield 10-cyclohexyl-4H-imidazo[1,2-a]indolo[1,2-d][1,4]benzodiazepine-7-carboxylic acid (47 mg, 0.12 mmol) as an off-white solid which was used without further purification. $^1$H NMR (500 MHz, $d_6$-DMSO) δ 1.04-1.22 (m, 1H), 1.32-1.50 (m, 3H), 1.61-1.77 (m, 2H), 1.84-2.15 (m, 4H), 2.74-2.90 (m, 1H), 5.05 (d, J=15.7 Hz, 1H), 6.00 (d, J=15.7 Hz, 1H), 7.31 (s, 1H), 7.63-7.85 (m, 5H), 7.91-7.99 (m, 2H), 8.37 (s, 1H). LCMS: m/e 398 (M+H)$^+$, ret time 1.87 min.

Example 6

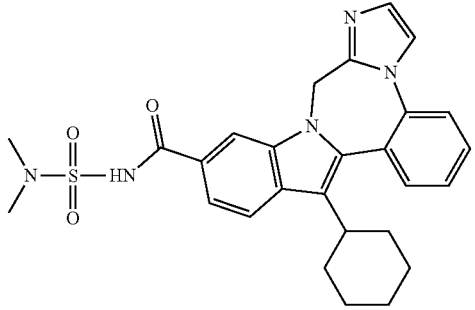 [SMILES: CN(C)S(=O)(=O)NC(=O)c1ccc2c(C3CCCCC3)c3n(c2c1)Cc1nccn1-c1ccccc1-3]

10-Cyclohexyl-N-((dimethylamino)sulfonyl)-4H-imidazo[1,2-a]indolo[1,2-d][1,4]benzodiazepine-7-carboxamide To a solution of 10-cyclohexyl-4H-imidazo[1,2-a]indolo[1,2-d][1,4]benzodiazepine-7-carboxylic acid (25 mg, 0.063 mmol) and N,N-dimethylsulfamide (41 mg, 0.33 mmol) in DMF (1.5 mL), was added DMAP (40 mg, 0.33 mmol) and then EDCI-HCl (50 mg, 0.26 mmol). The reaction mixture was stirred at 60° C. for 2 h, cooled to rt, diluted with DMSO and MeOH and purified by prep HPLC (MeOH/H$_2$O with 10 mM TFA buffer) to yield 10-cyclohexyl-N-((dimethylamino)sulfonyl)-4H-imidazo[1,2-a]indolo[1,2-d][1,4]benzodiazepine-7-carboxamide (5.4 mg, 0.011 mmol, 17%) as a bright yellow solid. $^1$H NMR (500 MHz, CD$_3$OD) δ 1.18-1.56 (m, 4H), 1.74-1.85 (m, 2H), 1.95-2.21 (m, 4H), 2.86-2.98 (m, 1H), 3.04 (s, 6H), 5.19 (d, J=16.1 Hz, 1H), 6.01 (d, J=16.1 Hz, 1H), 7.47 (d, J=2.2 Hz, 1H), 7.66 (dd, J=8.4, 1.5 Hz, 1H), 7.77-7.91 (m, 4H), 7.94 (d, J=1.8 Hz, 1H), 8.01 (d, J=8.4 Hz, 1H), 8.28 (s, 1H). LCMS: m/e 504 (M+H)$^+$, ret time 1.81 min.

Example 7

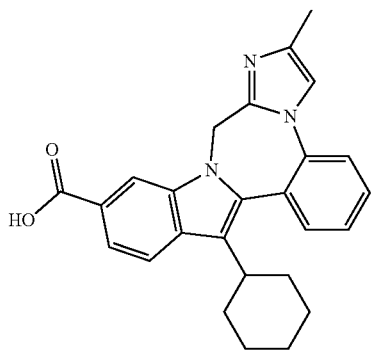 [SMILES: Cc1cn2c(n1)Cn1c(c(C3CCCCC3)c3ccc(C(=O)O)cc31)-c1ccccc1-2]

10-Cyclohexyl-2-methyl-4H-imidazo[1,2-a]indolo[1,2-d][1,4]benzodiazepine-7-carboxylic acid To a solution of methyl 10-cyclohexyl-2-methyl-4H-imidazo[1,2-a]indolo[1,2-d][1,4]benzodiazepine-7-carboxylate (74 mg, 0.17 mmol) in THF (3 mL) and MeOH (1.5 mL) was added aq NaOH (1.0N, 0.8 mL, 0.8 mmol). The reaction mixture was heated at 70° C. for 2 h, cooled to rt, neutralized with aq. HCl (1.0N, 0.8 mL, 0.8 mmol) and concentrated to dryness. The solid residue was dissolved into MeOH/DCM, insoluble material was removed by filtration and the filtrate was concentrated and dried under $N_2$ to yield crude 10-cyclohexyl-2-methyl-4H-imidazo[1,2-a]indolo[1,2-d][1,4]benzodiazepine-7-carboxylic acid (60 mg, 0.15 mmol, 86%) as an off-white solid which was used without further purification. $^1$H NMR (300 MHz, CD$_3$OD) δ 1.16-1.56 (m, 4H), 1.72-2.22 (m, 6H), 2.31 (s, 3H), 2.80-3.01 (m, 1H), 5.12 (d, J=16.1 Hz, 1H), 5.91 (d, J=16.1 Hz, 1H), 7.62 (s, 1H), 7.72-7.86 (m, 5H), 7.97 (d, J=8.8 Hz, 1H), 8.39 (s, 1H). LCMS: m/e 412 (M+H)$^+$, ret time 1.65 min.

Example 8

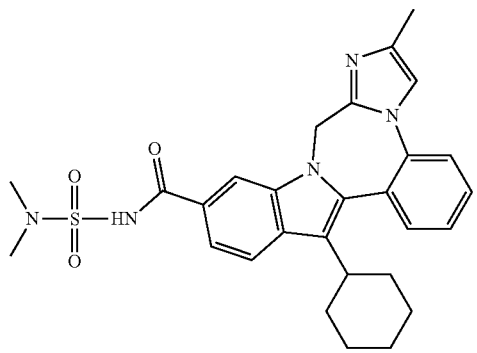 [SMILES: Cc1cn2c(n1)Cn1c(c(C3CCCCC3)c3ccc(C(=O)NS(=O)(=O)N(C)C)cc31)-c1ccccc1-2]

10-Cyclohexyl-N-((dimethylamino)sulfonyl)-2-methyl-4H-imidazo[1,2-a]indolo[1,2-d][1,4]benzodiazepine-7-carboxamide To a solution of 10-cyclohexyl-2-methyl-4H-imidazo[1,2-a]indolo[1,2-d][1,4]benzodiazepine-7-carboxylic acid (58 g, 0.14 mmol) and N,N-dimethylsulfamide (82 g, 0.66 mol) in DMF (2 mL) added DMAP (80 mg, 0.66 mmol) and then EDCI-HCl (100 mg, 0.52 mmol). The reaction mixture was stirred at 60° C. for 2 h, cooled to rt, diluted with DMSO and MeOH and purified by prep HPLC (MeOH/H$_2$O with 10 mM TFA buffer) to yield 10-cyclohexyl-N-((dimethylamino)sulfonyl)-2-methyl-4H-imidazo[1,2-a]indolo[1,2-d][1,4]benzodiazepine-7-carboxamide (32 mg, 0.062 mmol, 44%) as a pink solid. $^1$H NMR (300 MHz, CD$_3$OD) δ 1.14-1.32 (m, 1H), 1.36-1.57 (m, 3H), 1.73-1.85 (m, 2H), 1.94-2.20 (m, 4H), 2.34 (s, 3H), 2.84-2.98 (m, 1H), 3.04 (s, 6H), 5.20 (d, J=16.1 Hz, 1H), 5.97 (d, J=16.1 Hz, 1H), 7.66 (dd, J=8.6, 1.7 Hz, 1H), 7.71 (s, 1H), 7.77-7.90 (m, 4H), 8.01 (d, J=8.8 Hz, 1H), 8.27 (s, 1H). LCMS: m/e 518 (M+H)$^+$, ret time 1.80 min.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

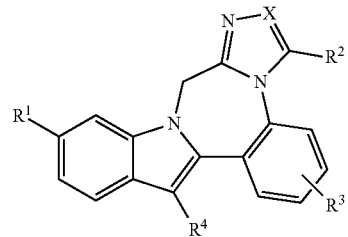

where:
$R^1$ is CO$_2$R$^5$ or CONR$^6$R$^7$;
$R^2$ is hydrogen or alkyl;
$R^3$ is hydrogen, halo, alkyl, alkenyl, hydroxy, benzyloxy, or alkoxy;
$R^4$ is cycloalkyl;
$R^5$ is hydrogen or alkyl;
$R^6$ is hydrogen, alkyl, alkylSO$_2$, cycloalkylSO$_2$, haloalkylSO$_2$, (R$^8$)(R$^9$)NSO$_2$, or (R$^{10}$)SO$_2$;
$R^7$ is hydrogen or alkyl;
$R^8$ is hydrogen or alkyl;
$R^9$ is hydrogen or alkyl;
$R^{19}$ is azetidinyl, pyrrolidinyl, piperidinyl, piperazinyl, N-(alkyl)piperazinyl, morpholinyl, thiomorpholinyl, homopiperidinyl, or homomorpholinyl;
$R^{11}$ is hydrogen or alkyl; and
X is N or CR$^{11}$
or a pharmaceutically acceptable salt thereof.

2. A compound of claim 1 where $R^1$ is CO$_2$R$^5$ or CONR$^6$R$^7$; $R^2$ is hydrogen or alkyl; $R^3$ is hydrogen; $R^4$ is cycloalkyl; $R^5$ is hydrogen; $R^6$ is (R$^8$)(R$^9$)NSO$_2$; R$^7$ is hydrogen; $R^8$ is alkyl; $R^9$ is alkyl; $R^H$ is hydrogen or alkyl; and X is N or CR$^{11}$; or a pharmaceutically acceptable salt thereof.

3. A compound of claim 2 where $R^1$ is CO$_2$H or CONHSO$_2$NMe$_2$; $R^2$ is hydrogen or methyl; $R^3$ is hydrogen; $R^4$ is cyclohexyl; and X is N, CH or CMe; or a pharmaceutically acceptable salt thereof.

4. A compound of claim 1 where $R^1$ is CONR$^6$R$^7$; $R^6$ is alkylSO$_2$, cycloalkylSO$_2$, haloalkylSO$_2$, (R$^8$)(R$^9$)NSO$_2$, or (R$^1$)SO$_2$; and R$^7$ is hydrogen.

5. A compound of claim 1 where $R^3$ is hydrogen.

6. A compound of claim 1 where $R^3$ is methoxy.

7. A compound of claim 1 where $R^4$ is cyclohexyl.

8. A compound of claim 1 where $R^6$ is $(R^8)(R^9)_2NSO_2$ or $(R^{10})SO_2$.

9. A compound of claim 1 where X in N.

10. A compound of claim 1 where X is $CR^{11}$.

11. A compound of claim 1 selected from the group consisting of

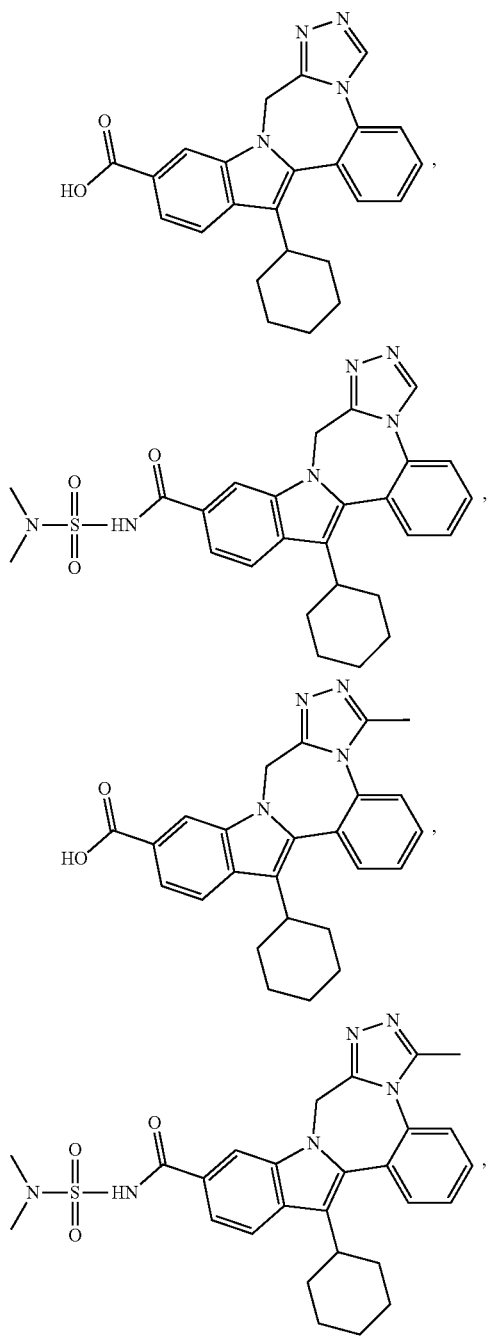

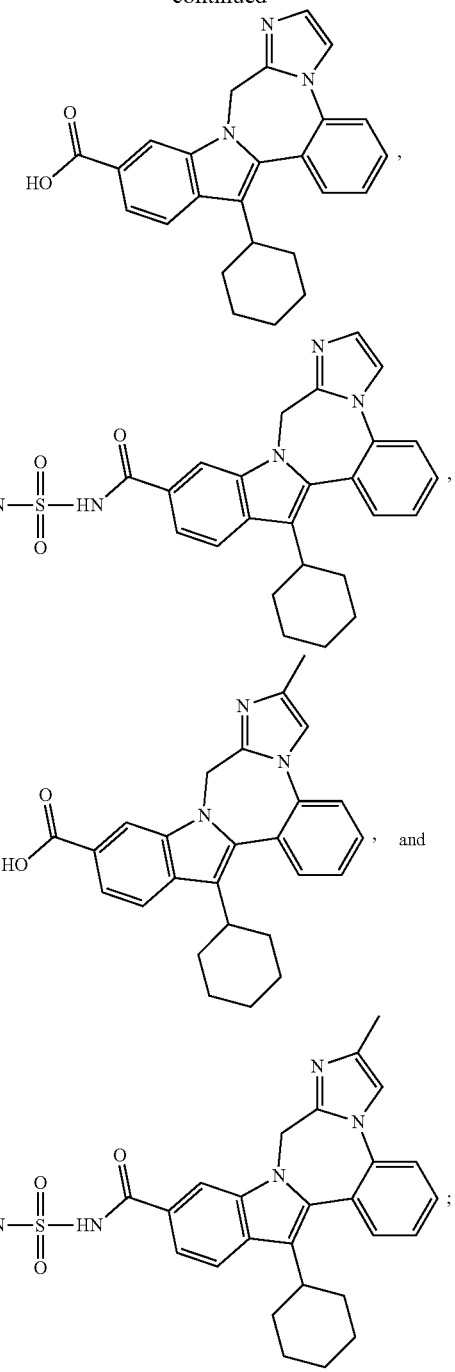

or a pharmaceutically acceptable salt thereof.

12. A composition comprising a compound of claim 1, or a pharmaceutically acceptable salt thereof, and a pharmaceutically acceptable carrier.

13. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 8,431,568 B2  Page 1 of 1
APPLICATION NO. : 12/922801
DATED : April 30, 2013
INVENTOR(S) : John A. Bender et al.

It is certified that error appears in the above-identified patent and that said Letters Patent is hereby corrected as shown below:

In the Claims:

Claim 1:

Column 30, line 48, change "$R^{19}$" to -- $R^{10}$ --.

Claim 2:

Column 30, line 57, change "$R^{H}$" to -- $R^{11}$ --.

Claim 4:

Column 30, lines 64 and 65, change "or) $(R^1)SO_2$;" to -- or $(R^{10})SO_2$; --.

Claim 8:

Column 31, line 3, change "or)$(R^{10})SO_2$." to -- or $(R^{10})SO_2$. --.

Signed and Sealed this
Twenty-ninth Day of April, 2014

Michelle K. Lee
*Deputy Director of the United States Patent and Trademark Office*